(12) United States Patent
Arnoldussen

(10) Patent No.: US 8,968,279 B2
(45) Date of Patent: Mar. 3, 2015

(54) SYSTEMS AND METHODS FOR QUALIFYING AND CALIBRATING A BEAM DELIVERY SYSTEM

(75) Inventor: Mark E. Arnoldussen, San Carlos, CA (US)

(73) Assignee: AMO Manufacturing USA, LLC, Santa Anna, CA (US)

( * ) Notice: Subject to any disclaimer, the term of this patent is extended or adjusted under 35 U.S.C. 154(b) by 2771 days.

(21) Appl. No.: 11/339,984

(22) Filed: Jan. 25, 2006

(65) Prior Publication Data
US 2007/0173792 A1 Jul. 26, 2007

(51) Int. Cl.
*A61F 9/008* (2006.01)

(52) U.S. Cl.
CPC ............. *A61F 9/008* (2013.01); *A61F 9/00804* (2013.01); *A61F 9/00817* (2013.01); *A61F 2009/00855* (2013.01); *A61F 2009/00872* (2013.01); *A61F 2009/00897* (2013.01)
USPC .............................................. 606/4; 351/246

(58) Field of Classification Search
CPC .......................... A61F 9/008; A61F 2009/008
See application file for complete search history.

(56) References Cited

U.S. PATENT DOCUMENTS

| | | | |
|---|---|---|---|
| 4,665,913 A | 5/1987 | L'Esperance, Jr. | |
| 4,669,466 A | 6/1987 | L'Esperance | |
| 4,732,148 A | 3/1988 | L'Esperance, Jr. | |
| 4,770,172 A | 9/1988 | L'Esperance, Jr. | |
| 4,773,414 A | 9/1988 | L'Esperance, Jr. | |
| 4,777,637 A | 10/1988 | Hayashi et al. | |
| 4,901,718 A * | 2/1990 | Bille et al. | 606/4 |
| 5,108,388 A | 4/1992 | Trokel | |
| 5,144,630 A | 9/1992 | Lin | |
| 5,163,934 A | 11/1992 | Munnerlyn | |
| 5,196,006 A | 3/1993 | Klopotek et al. | |
| 5,207,668 A | 5/1993 | L'Esperance, Jr. | |
| 5,219,343 A | 6/1993 | L'Esperance, Jr. | |

(Continued)

FOREIGN PATENT DOCUMENTS

| | | |
|---|---|---|
| WO | WO 99/04220 A | 1/1999 |
| WO | WO 00/41639 A | 7/2000 |

(Continued)

OTHER PUBLICATIONS

PCT International Search Report and Written Opinion mailed Jul. 6, 2007; International Application No. PCT/US2007/002319, 11 pages.

*Primary Examiner* — Lynsey Crandall
(74) *Attorney, Agent, or Firm* — Kilpatrick Townsend & Stockton LLP

(57) ABSTRACT

Systems and methods for testing a laser eye surgery system are provided. Methods include establishing an image scale based on a calibration pattern, imageably altering a series of regions of a test surface with the laser system, laterally redirecting a laser beam to form a test pattern, imaging the test pattern, determining a lateral redirecting characteristic of the beam delivery system, and qualifying or calibrating the beam delivery system. Systems can include an input module that accepts an input member such as a calibration pattern parameter, a calibration pattern image, an intended pattern parameter, a test pattern image, an imaging device position, a calibration pattern position, a test pattern position, and a beam delivery system position, a characterization module that determines a beam delivery system characteristic, and an output module that generates a calibration for the beam delivery system of the laser eye surgery system.

8 Claims, 10 Drawing Sheets

(56) References Cited

U.S. PATENT DOCUMENTS

| | | |
|---|---|---|
| 5,323,229 A | 6/1994 | May et al. |
| 5,520,679 A | 5/1996 | Lin |
| 5,556,395 A | 9/1996 | Shimmick et al. |
| 5,624,436 A | 4/1997 | Nakamura et al. |
| 5,630,810 A | 5/1997 | Machat |
| 5,646,791 A | 7/1997 | Glockler |
| 5,742,626 A | 4/1998 | Mead et al. |
| 5,772,656 A | 6/1998 | Klopotek |
| 5,782,822 A | 7/1998 | Telfair et al. |
| 6,008,904 A | 12/1999 | Ishii et al. |
| 6,080,144 A | 6/2000 | O'Donnell, Jr. |
| 6,090,102 A | 7/2000 | Telfair et al. |
| 6,116,737 A | 9/2000 | Kern |
| 6,195,164 B1 | 2/2001 | Thompson |
| 6,245,058 B1 | 6/2001 | Suzuki |
| 6,245,059 B1 | 6/2001 | Clapham |
| 6,251,101 B1 | 6/2001 | Glockler |
| 6,268,921 B1 | 7/2001 | Seitz et al. |
| 6,271,914 B1 | 8/2001 | Frey et al. |
| 6,322,216 B1 | 11/2001 | Yee et al. |
| 6,322,555 B1 | 11/2001 | LaHaye |
| 6,331,177 B1 | 12/2001 | Munnerlyn et al. |
| 6,369,898 B1 | 4/2002 | Van Saarloos et al. |
| 6,392,756 B1 | 5/2002 | Li et al. |
| 6,454,761 B1 | 9/2002 | Freedman |
| 6,559,934 B1 | 5/2003 | Yee et al. |
| 6,562,026 B2 | 5/2003 | Glockler |
| 6,666,855 B2 | 12/2003 | Somani et al. |
| 6,816,316 B2 | 11/2004 | Caudle et al. |
| 6,817,998 B2 | 11/2004 | LaHaye |
| 7,001,375 B2 | 2/2006 | Yee et al. |
| 7,001,376 B2 | 2/2006 | Somani et al. |
| 7,196,800 B1 | 3/2007 | Birdsley et al. |
| 7,238,177 B2 | 7/2007 | Somani et al. |
| 2002/0026181 A1 | 2/2002 | O'Donnell, Jr. |
| 2002/0198515 A1 * | 12/2002 | Somani et al. ............ 606/4 |
| 2003/0028115 A1 * | 2/2003 | Thomas .................. 600/476 |
| 2003/0107742 A1 | 6/2003 | Tualle |
| 2004/0102764 A1 | 5/2004 | Balling |
| 2005/0094249 A1 | 5/2005 | Imajaku et al. |
| 2005/0094262 A1 | 5/2005 | Spediacci et al. |
| 2005/0122572 A1 | 6/2005 | Campbell et al. |
| 2005/0215986 A1 | 9/2005 | Chernyak et al. |
| 2007/0173797 A1 | 7/2007 | Zickler |

FOREIGN PATENT DOCUMENTS

| | | |
|---|---|---|
| WO | WO 02/76319 | 3/2002 |
| WO | WO 02/33350 A | 4/2002 |
| WO | WO 03/068103 A | 8/2003 |

* cited by examiner

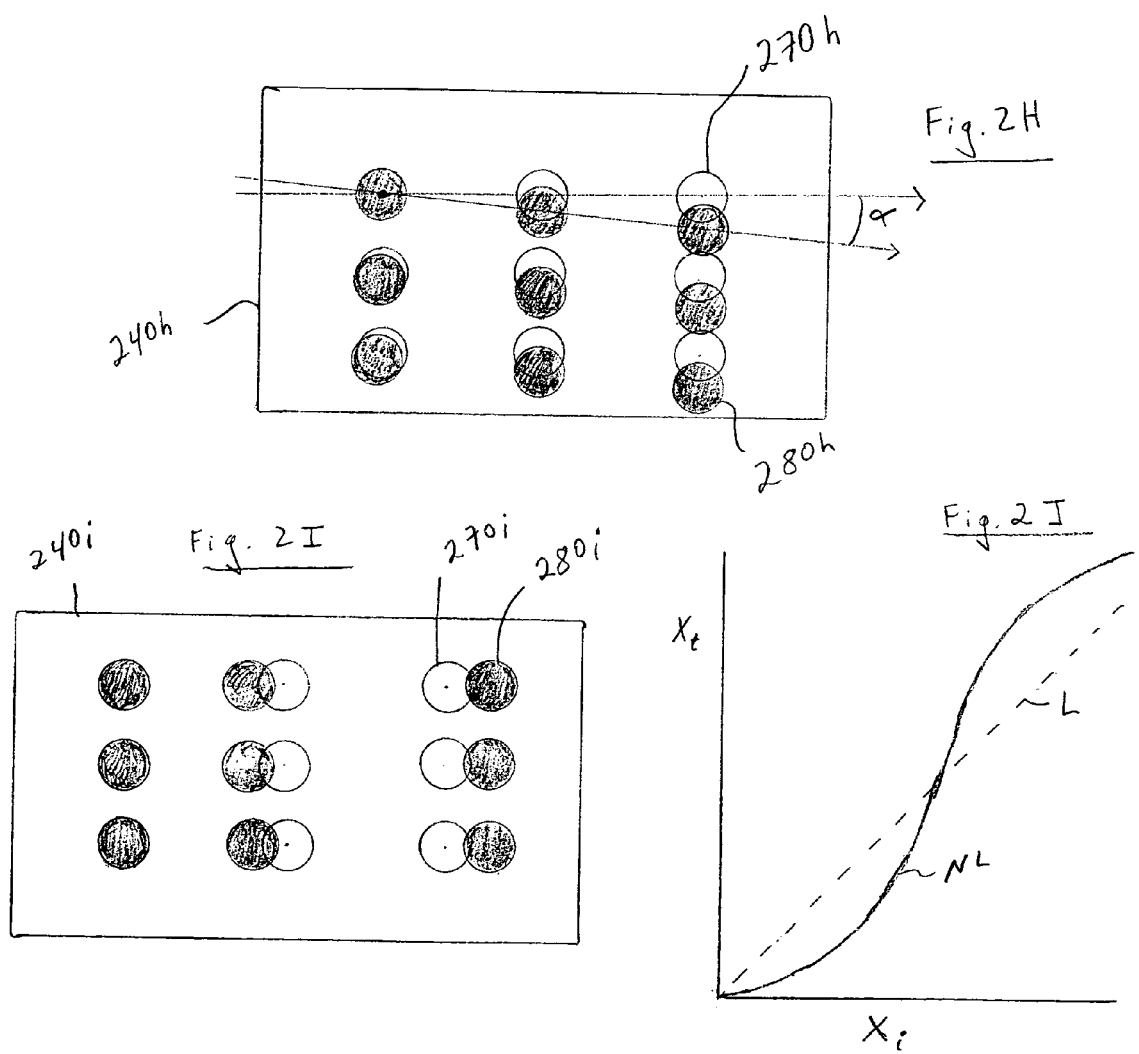

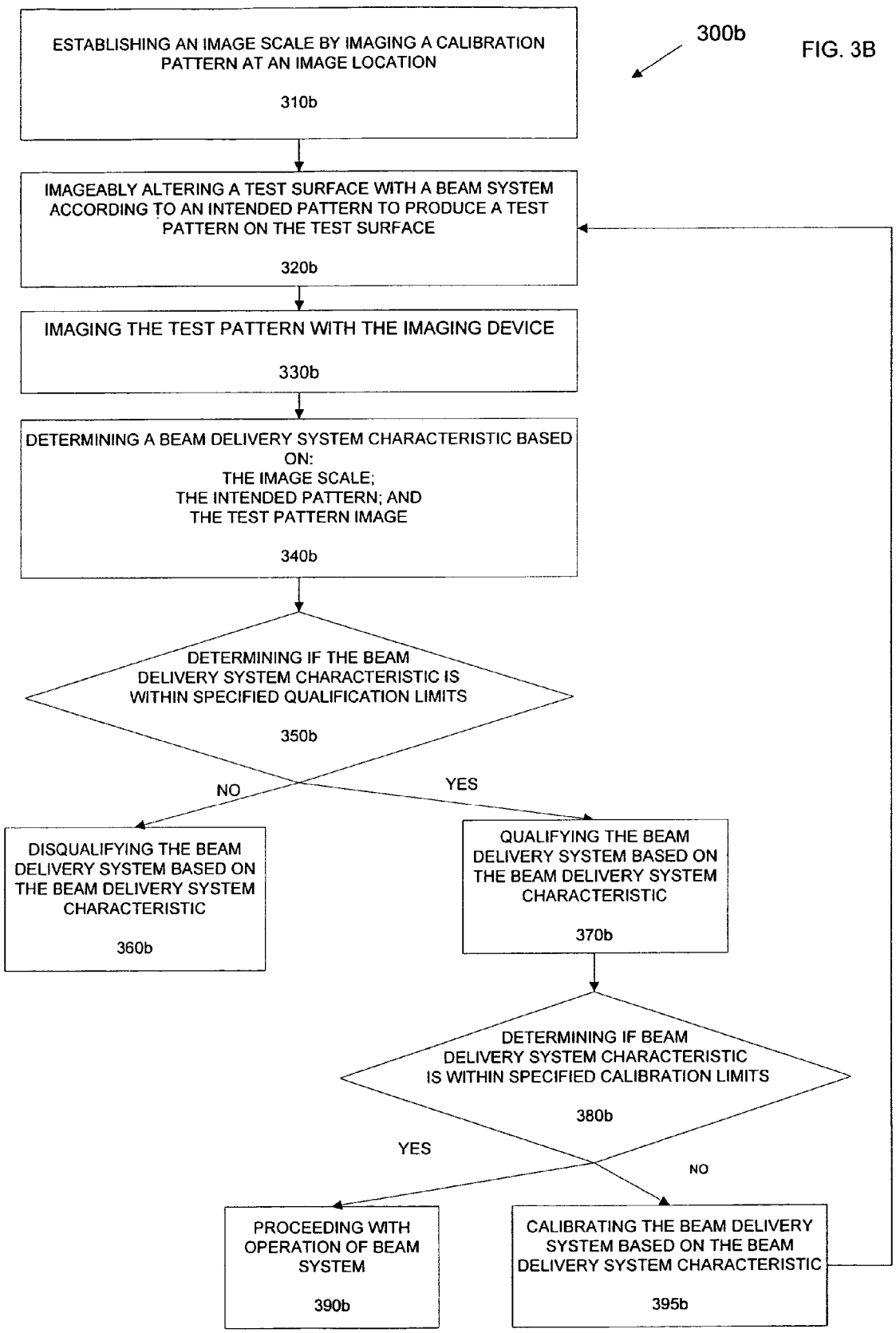

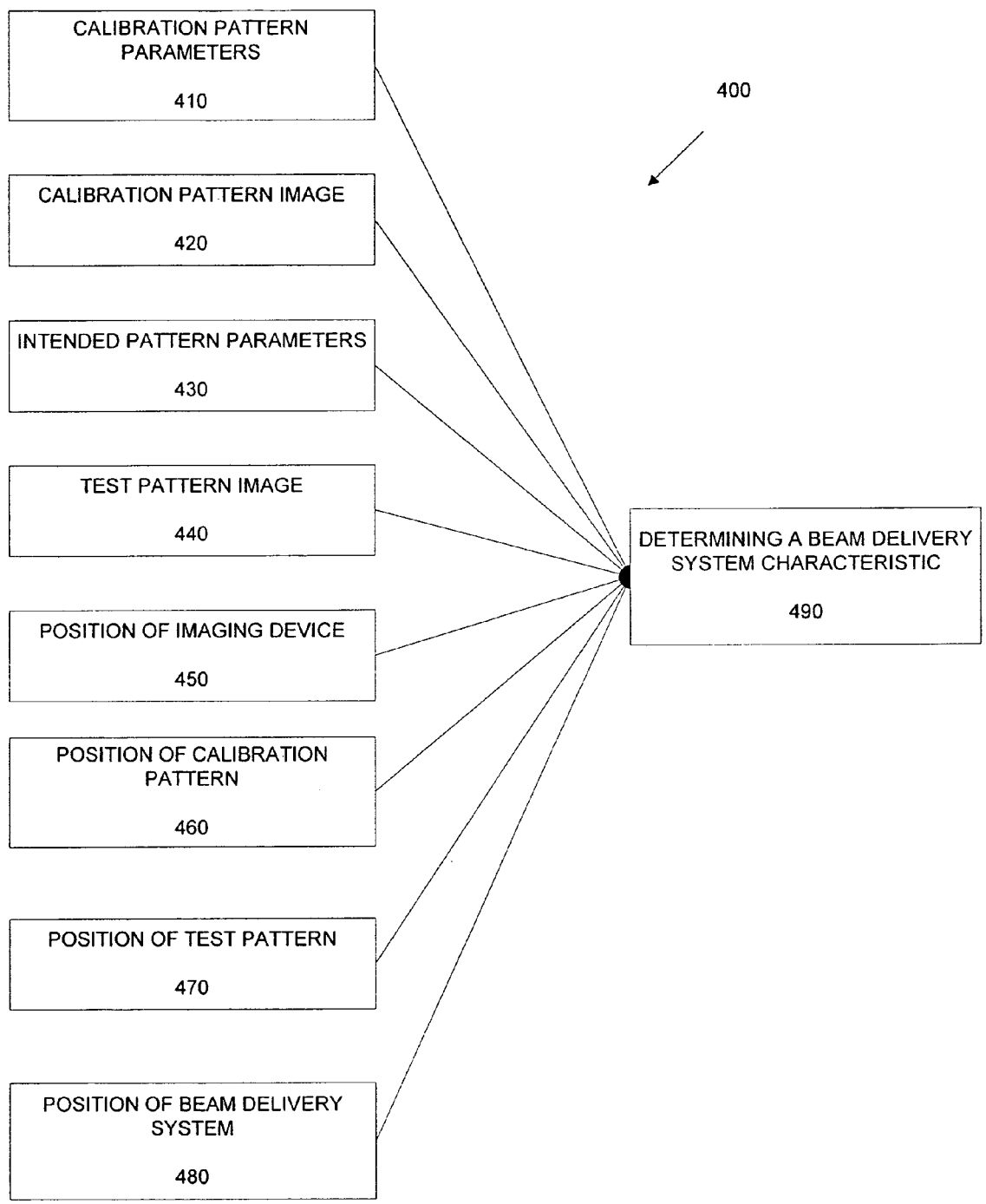

SYSTEMS AND METHODS FOR QUALIFYING AND CALIBRATING A BEAM DELIVERY SYSTEM

CROSS-REFERENCES TO RELATED APPLICATIONS

This application is related to U.S. Pat. Nos. 6,195,164, 6,559,934, 6,666,855; and to U.S. patent application Ser. No. 10/383,445 filed Mar. 6, 2003; Ser. No. 10/085,253 filed Oct. 13, 2003; Ser. No. 11/264,785 filed Oct. 31, 2005; and Ser. No. 10/808,728 filed Mar. 24, 2004, the full disclosures of which are hereby incorporated by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates generally to methods and systems for qualifying and calibrating beam delivery systems. More specifically, embodiments of the present invention relate to methods and systems for qualifying and calibrating a opthalmological surgery laser beam delivery system based on a laser beam delivery system characteristic.

Laser based systems are commonly used in opthalmological surgery on corneal tissues of the eye to correct vision defects. These systems use lasers to achieve a desired change in corneal shape, with the laser removing microscopic layers of stromal tissue from the cornea using a technique generally described as ablative photodecomposition to alter the refractive characteristics of the eye. Laser eye surgery techniques are useful in procedures such as photorefractive keratotomy (PRK), phototherapeutic keratectomy (PTK), laser in situ keratomileusis (LASIK), and the like.

Laser ablation procedures can reshape or sculpt the shape of the cornea for varying purposes, such as for correcting myopia, hyperopia, astigmatism, and other corneal surface profile defects. In known systems, the laser beam often comprises a series of discrete pulses of laser light energy, with the total shape and amount of tissue being removed being determined by the position, shape, size, and/or number of a pattern of laser energy pulses impinging on the cornea. A variety of algorithms may be used to calculate the pattern of laser pulses used to reshape the cornea so as to correct a refractive error of the eye.

Accurate control of the laser beam delivery system is crucial for patient safety and successful vision correction. Accordingly, laser beam delivery systems are qualified and calibrated to ensure control over the positioning and distribution of ablation energy across the cornea so as to minimize undesirable laser system performance, which may result from flawed internal mechanical or optical components, misalignment, and the like. In particular, qualification and calibration of the laser system helps ensure accurate removal of the intended shape and quantity of the corneal tissue so as to provide the desired shape and refractive power modification to the patient's cornea. Imprecise control of the laser beam may jeopardize the success of the surgery and could cause damage to the patient's eye. For example, deviation from a desired laser beam path or position may result in tissue ablation at an undesired location on the patient's cornea which in turn leads to less than ideal corneal sculpting results. As such, it is beneficial to provide precise control over the positioning of the laser beam so as to accurately sculpt the patient's cornea through laser ablation.

In light of the above, it would be desirable to provide improved methods and systems for qualifying and calibrating beam delivery systems on the basis of beam path positioning and other related beam path and beam delivery system characteristics. It would be further desirable if such methods and systems enhanced qualification and calibration accuracy without significantly increasing the overall system cost and complexity. At least some of these objectives will be met by the methods and systems described herein.

BRIEF SUMMARY OF THE INVENTION

Method and system embodiments are provided for qualifying and calibrating a beam delivery system, such as an excimer laser system for selectively ablating a cornea of a patient's eye. In particular, improved methods and systems are provided for laser beam positioning using an image capture device such as a microscope camera. Such methods and systems further provide enhanced qualification and calibration accuracy and precision without significantly increasing the overall system cost and complexity and may be applied to a variety of laser systems. Each of the methods described herein may be performed using system computers or modules having any of a wide variety of digital and/or analog data processing hardware and/or software.

In a first aspect, an exemplary embodiment includes a method of testing a laser eye surgery system. The method includes imaging a known calibration pattern at an image location with an imaging device, establishing an image scale based on the calibration pattern and the calibration pattern image, imageably altering a series of regions of a test surface with a laser beam of the laser eye surgery system at the imaging location, laterally redirecting the laser beam according to an intended pattern between altering of the regions using a beam delivery system so as to form a test pattern on the test surface, imaging the test pattern at the imaging location with the imaging device, and determining a lateral redirecting characteristic of the beam delivery system based on the image scale, the intended pattern, and the test pattern image. The method may also include qualifying or calibrating the beam delivery system in response to the lateral redirecting characteristic.

In some embodiments, the beam delivery system laterally redirects the beam along a first axis from a first region to a second region, and laterally redirects the beam along the first axis from the second region to a third region. The beam delivery system can be calibrated by altering machine readable code of the laser eye surgery system so that a subsequent lateral deflection of the beam between the first region and the second region is determined using a first calibration factor, and so that a subsequent lateral deflection of the beam between the second region and the third region is determined using a second calibration factor, where the second calibration factor is different than the first calibration factor. In related embodiments, the beam delivery system laterally redirects the beam along a second axis a plurality of times, and the beam delivery system is calibrated by altering the machine readable code of the laser eye surgery system so that subsequent lateral deflections of the beam along the second axis are determined using a plurality of different calibration factors associated with different beam locations along the second axis, where the second axis intersecting the first axis.

In some embodiments, the beam delivery system laterally redirects the beam along a first axis from a first region to a second region, and laterally redirects the beam along a second axis from the second region to a third region. The beam delivery system can be calibrated by altering machine readable code of the laser eye surgery system so that a subsequent lateral deflection of the beam along the first axis is determined using a first calibration factor, and so that a subsequent lateral deflection of the beam along the second axis is determined using a second calibration factor, where the second calibration factor is different than the first calibration factor. In some embodiments, the beam delivery system laterally redirects the beam along a first test pattern axis of the test pattern from a first region to a second region, and the qualifying or calibrating of the beam includes identifying an offset between the test pattern axis and an intended axis of the intended pattern. Calibrating the beam can include altering machine readable code of the laser eye surgery system so that a subsequent lateral deflection of the beam along the first test pattern axis is determined based on the offset. Qualifying the beam can include enabling use of the laser eye surgery system in response to the offset being below an acceptable tolerance. In some cases, the offset includes an angular offset.

In some embodiments, the beam delivery system laterally redirects the beam along a first test pattern vector between the regions of the test pattern, and laterally redirects the beam along a second test pattern vector between the regions of the test pattern. Qualification or calibration of the beam delivery system can include determining offsets between the vectors and intended vectors between regions of the intended pattern. In some embodiments, the method may include calibrating the laser eye system by altering machine readable code of the laser eye surgery system in response to a first lateral beam deflecting characteristic of the beam delivery system, and qualifying the laser eye surgery system by enabling use of the laser eye surgery system in response to a second lateral beam deflecting characteristic of the beam delivery system being within an acceptable threshold tolerance.

In another aspect, embodiments include a method of qualifying a laser eye surgery system. The method can include imaging a calibration pattern at an image location with an imaging device, establishing an image scale based on the calibration pattern and the calibration pattern image, imageably altering a test surface with a beam delivery system according to an intended pattern to produce a test pattern on the test surface, imaging the test pattern with the imaging device, and determining a beam delivery system characteristic based on the image scale, the intended pattern, and the test pattern image. The method can also include qualifying the laser eye surgery system if the beam delivery system characteristic satisfies a specified qualification limit. In some aspects, the method can include disqualifying the laser eye surgery system if the beam delivery system characteristic exceeds a specified qualification limit. In some aspects, the method can include calibrating the laser eye surgery system if the beam delivery system characteristic exceeds a specified calibration limit. In a related aspect, the test pattern image can include a test spot image, and determination of the beam delivery system characteristic can be based on a centroid calculated for the test spot image. In some aspects, the beam delivery system characteristic includes a member selected from the group consisting of a scaling calibration, a rotational offset, an axial deflection offset, a pincushion offset, a mirror thickness offset, an alignment offset, a tilt, and a warping factor. In some aspects, the beam delivery system can include a plurality of galvanometer-controlled mirrors.

In another aspect, embodiments provide a computer program product for calibrating a beam delivery system of a laser eye surgery system. The computer program product can include code for accepting a calibration pattern image, code for establishing an image scale based on the calibration pattern image, code for accepting an intended pattern, code for accepting a test pattern image, code for determining a beam delivery system characteristic based on the image scale, the intended pattern, and the test pattern image, and code for calibrating the beam delivery system based on the beam delivery system characteristic. In some embodiments, the code for calibrating the beam delivery system includes code for adjusting a signal correlation in the beam delivery system. In related embodiments, the test pattern image includes a test spot image, and the code for determining a beam delivery system characteristic includes a code for calculating a centroid of the test spot image. In some embodiments, the centroid for the test spot image of size is calculated as $$C_x = \frac{\frac{1}{K}\sum_{j=1}^{J}\sum_{k=1}^{K} x_k F(j,k)}{\sum_{j=1}^{J}\sum_{k=1}^{K} F(j,k)},$$

$$C_y = \frac{\frac{1}{K}\sum_{j=1}^{J}\sum_{k=1}^{K} y_j F(j,k)}{\sum_{j=1}^{J}\sum_{k=1}^{K} F(j,k)},$$

where $\{C_x, C_y\}$ represents the centroid and $F(j,k)$ represents the test spot image of size $J \times K$.

In another aspect, embodiments of the present invention provide a system for calibrating a beam delivery system of a laser eye surgery system. The system can include an input module that accepts an input member selected from the group consisting of a calibration pattern parameter, a calibration pattern image, an intended pattern parameter, a test pattern image, an imaging device position, a calibration pattern position, a test pattern position, and a beam delivery system position. The system can also include a characterization module that determines a beam delivery system characteristic based on the input member; and an output module that generates a calibration for the beam delivery system of the laser eye surgery system based on the beam delivery system characteristic. In some embodiments, the beam delivery system characteristic can include a member selected from the group consisting of a scaling calibration, a rotational offset, an axial deflection offset, a pincushion offset, a mirror thickness offset, an alignment offset, a tilt, and a warping factor. In related embodiments, the calibration can include a signal correlation adjustment. In some embodiments, the test pattern image includes a test spot image, and the characterization module determines the beam delivery system characteristic based on a centroid calculated for the test spot image. In related embodiments, the centroid for the test spot image of size is calculated as $$C_x = \frac{\frac{1}{K}\sum_{j=1}^{J}\sum_{k=1}^{K} x_k F(j,k)}{\sum_{j=1}^{J}\sum_{k=1}^{K} F(j,k)},$$

$$C_y = \frac{\frac{1}{K}\sum_{j=1}^{J}\sum_{k=1}^{K} y_j F(j,k)}{\sum_{j=1}^{J}\sum_{k=1}^{K} F(j,k)},$$

where $\{C_x, C_y\}$ represents the centroid and $F(j,k)$ represents the test spot image of size J×K.

BRIEF DESCRIPTION OF THE DRAWINGS

FIGS. 2A, 2B, 2C, 2D, 2E, 2F, 2G, 2H, 2I, 2J, 2K, and 2L illustrate exemplary techniques for qualifying and calibrating a beam delivery system according to embodiments of the present invention.

FIGS. 3A and 3B illustrate exemplary methods for qualifying and calibrating a beam delivery system according to embodiments of the present invention.

FIG. 4 illustrates an exemplary method for determining a beam delivery system characteristic according to one embodiment of the present invention.

DETAILED DESCRIPTION OF THE INVENTION

Methods and systems are provided for qualifying and calibrating a beam delivery system, such as an excimer laser system for selectively ablating a cornea of a patient's eye. In particular, improved methods and systems are provided for laser beam positioning using an image capture device, such as a microscope camera, for enhanced qualification and calibration accuracy and precision. By qualifying and calibrating a beam delivery system, a desired corneal ablation treatment can be accurately effected without the beam becoming incident on undesired locations of corneal tissue. Methods and systems may be utilized upon replacement, maintenance, installation, evaluation, or trouble-shooting of any beam delivery system component, e.g., internal mechanical or optical components such as a mirror or an iris, major optical re-alignment of the system, or problems with error generation. In some aspects, these techniques may be useful in periodic maintenance that is performed on a beam system, for example, according to an annual maintenance schedule. These techniques may also be useful during system manufacturing, initial system set-up, or field servicing. As used herein, the term "calibration" encompasses altering or configuring machine readable code or programming instructions for a beam delivery system. The term "qualification" encompasses determining that a system, subsystem, or component is within an acceptable tolerance.

Figure 1A:
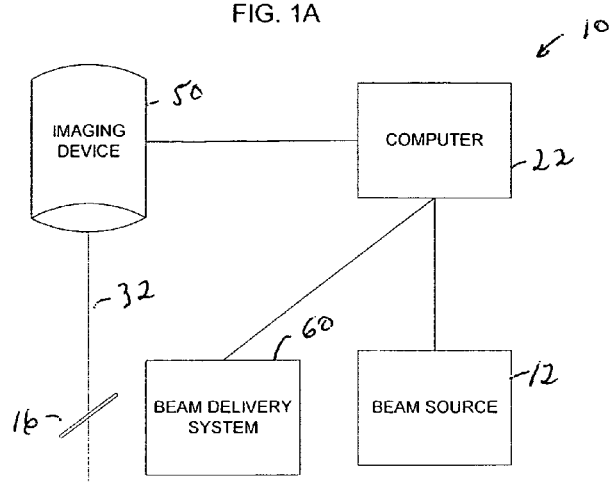
FIGS. 1A, 1B, 1C, 1D, and 1E illustrate exemplary systems for qualifying and calibrating a beam delivery system according to embodiments of the present invention.

FIG. 1A schematically illustrates an exemplary system 10 embodiment for qualifying and calibrating a beam delivery system 60. System 10 is particularly useful for qualifying and calibrating a laser ablation system of the type used to ablate a region of the cornea in a surgical procedure, such as an excimer laser used in photorefractive keratotomy (PRK), photo-therapeutic keratectomy (PTK), laser in situ keratomileusis (LASIK), and the like. System 10 generally includes a beam source 12, a beam delivery system 60, a surface such as a photochromic mirror 16, a calibration pattern 30 disposed at an image location 18, an imaging device 50, and a computer 22. In some embodiments, beam source 12 or mirror 16 may be integral to or otherwise included in beam delivery system 60, and therefore the qualifying and calibrating techniques described herein may be applicable to these components as well. Calibration pattern 30 can be positioned along an imaging optical path 32 via a hinged support arm or mechanism 34 that allows or controls movement or orientation of calibration pattern 30 in three dimensional space relative to imaging device 50. In some case, calibration pattern 30 is rigidly fixed relative to imaging device 50 or other components of system 10. Calibration pattern 30 can be imaged by imaging device 50 to establish an image scale. Calibration pattern 30 can then be removed from imaging optical path 32. In some cases, an image scale represents a correlation between pixels or sensors of imaging device 50 and distance at image location 18 or measurement plane. Image location 18 or measurement plane often corresponds to a treatment or ablation plane. Imaging device 50 may include one or more pixels or sensors, in combination with one or more mechanical or optical elements such as a lens. It will be appreciated that the depictions herein are for illustrative purposes only and do not necessarily reflect the actual shape, size, or dimensions of system 10.

Figure 1B:
Figure 1C:
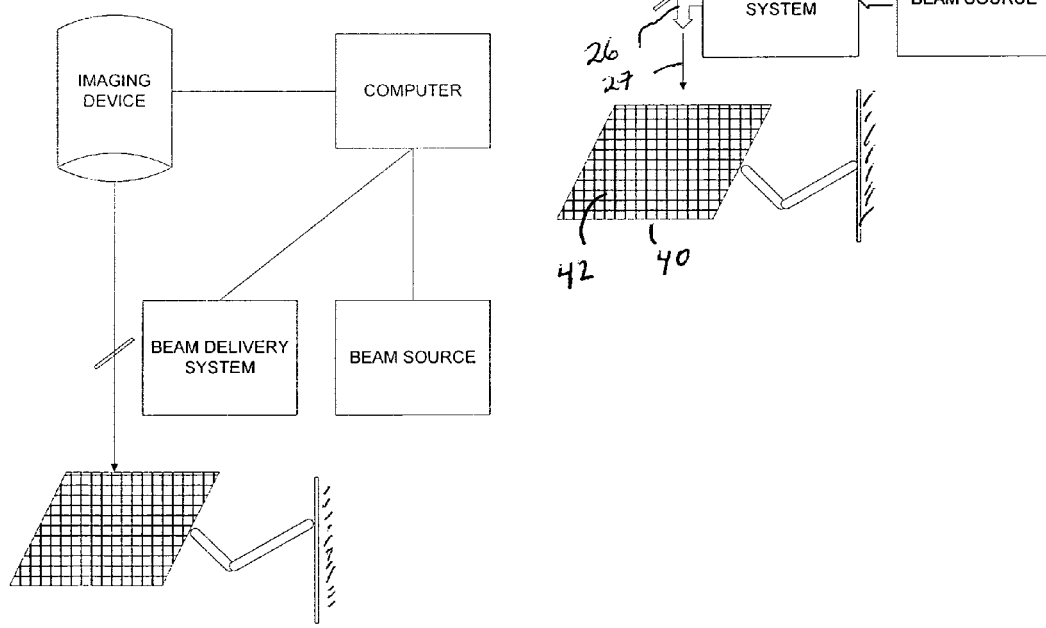

As illustrated in FIG. 1B, beam source 12 typically directs a beam 24 through beam delivery system 60 which in turn directs a positioned beam 26 according to a predetermined intended pattern. Positioned beam is reflected from mirror 16 toward a test surface 40, so as to create a test pattern 42 thereon. Test surface often corresponds to a treatment or ablation plane, and may also correspond to the distance at image location 18 or measurement plane. In some cases, when directed toward test surface 40, positioned beam 26 travels along an incident beam path 27 which is coaxial or substantially coaxial with imaging optical path 32. Beam path 27 may also be angularly offset with respect to imaging optical path 32. As shown in FIG. 1C, test pattern 42 is imaged by imaging device 50. Computer 22 can determine a qualification and calibration of beam delivery system 60 based on the image scale, the intended pattern, and the test pattern image, or on any of a variety of variables or parameters as discussed elsewhere herein. In some embodiments, calibration of beam delivery system 60 can involve or provide the basis for scaling or scaling transformations of lateral redirecting characteristics of beam delivery system 60. In some embodiments, qualification can be determined on the basis of whether a beam delivery system characteristic, such as a lateral redirecting characteristic, meets a specified tolerance. For example, a laser eye surgery system may be enabled for use in response to an offset being below an acceptable tolerance.

Computer or programmable processor 22 generally includes a processor, random access memory, tangible medium for storing instructions, a display, and/or other storage media such as hard or floppy drives. Processor 22 may include (or interface with) a conventional PC system including the standard user interface devices such as a keyboard, a display monitor, and the like. Processor 22 may include an input device such as a magnetic or optical disk drive, an internet connection, or the like. Such input devices can be used to download a computer executable code from a tangible storage media embodying any of the methods described herein. Tangible storage media may take the form of a floppy disk, an optical disk, a data tape, a volatile or non-volatile memory, RAM, or the like, and the processor may include the memory boards and other standard components of modern computer systems for storing and executing this code. Although tangible storage media will often be used directly in cooperation with a input device of processor 22, the storage media may also be remotely operatively coupled with processor by means of network connections such as the internet, and by wireless methods such as infrared, Bluetooth, or the like.

Relatedly, each of the calculations or operations described herein may be performed using computer 22, which may be a stand-along general purpose computer, or the like, having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described herein. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. In some embodiments, code may be downloaded from a communication modality such as the Internet, and stored as hardware, firmware, or software, or the like.

Beam source 12 may include, but is not limited to, an excimer laser such as an argon-fluoride excimer laser producing laser energy with a wavelength of about 193 nm. Alternative lasers may include solid state lasers, such as frequency multiplied solid state lasers, flash-lamp and diode pumped solid state lasers, and the like. Exemplary solid state lasers include ultraviolet solid state lasers producing wavelengths of approximately 188-240 nm such as those disclosed in U.S. Pat. Nos. 5,144,630, and 5,742,626; and in Borsutzky et al., "*Tunable UV Radiation at Short Wavelengths (188-240 nm) Generated by Sum-Frequency Mixing in Lithium Borate*" *Appl. Phys. B*, 52, 380-384 (1991), the full disclosures of which are incorporated herein by reference. A variety of alternative lasers might also be used, such as infrared or femtosecond lasers. For example, a pulsed solid state laser emitting infrared light energy may be used as described in U.S. Pat. Nos. 6,090,102 and 5,782,822, the full disclosures of which are incorporated herein by reference. The laser energy generally comprises a beam formed as a series of discrete laser pulses, and the pulses may be separated into a plurality of beamlets as described in U.S. Pat. No. 6,331,177, the full disclosure of which is incorporated herein by reference. Further exemplary beam systems and methods are described in U.S. Pat. Nos. 4,665,913; 4,669,466; 4,732,148; 4,770,172; 4,773,414; 5,163,934; and 5,556,395, the disclosures of which are hereby incorporated by reference in their entireties for all purposes. In an exemplary embodiment, a VISX STAR Excimer Laser System™, commercially available from VISX, Incorporated of Santa Clara, Calif., may be used for the ablation. This system can produce an output of 193.0 nm, operates at a frequency of 6.0 Hz and can be adjusted to deliver uniform fluence of 160.0 millijoules/$cm^2$ with a 6.0 mm diameter ablation zone. Other laser systems suitable for use may include the T-PRK™ scanning and tracking laser from Autonomous Technologies Corporation, the SVS Apex™ laser from Summit Technology Inc., the Keracor™ 117 scanning laser system from Chiron Vision, or the like. In addition to the beam types described above, it is appreciated that any of a variety of energy streams or radiation beams such as ultraviolet, gamma, and x-ray beams may be used.

In some embodiments, imaging device 50 can be exemplified by a microscope camera. In a related embodiment, imaging device 50 can include a camera having an image sensor such as a charge-couple device (CCD) or a complimentary metal oxide semiconductor (CMOS) digital image sensor. Relatedly, imaging device 50 may include an infrared sensitive CCD. It is appreciated that in some embodiments, system 10 may include more than one imaging device 50. Imaging device 50 may make use of at least a portion of the optics of a beam delivery system, such as with an on-axis or near on-axis viewing arrangement integrated into a microscope. In some cases, imaging device 50 may be entirely separate and/or off axis, optionally using off-axis tracking cameras. Imaging device 50 may also be coupled with or include a video system so as to enable a system operator to observe various steps of the qualification and calibration procedures. Some examples of imaging device 50 are described in U.S. Pat. Nos. 6,251,101; 6,322,216; and 6,562,026; and in U.S. Patent Publication No. 2005/0094262, the entire disclosures of which are hereby incorporated by reference for all purposes.

Figure 1D:
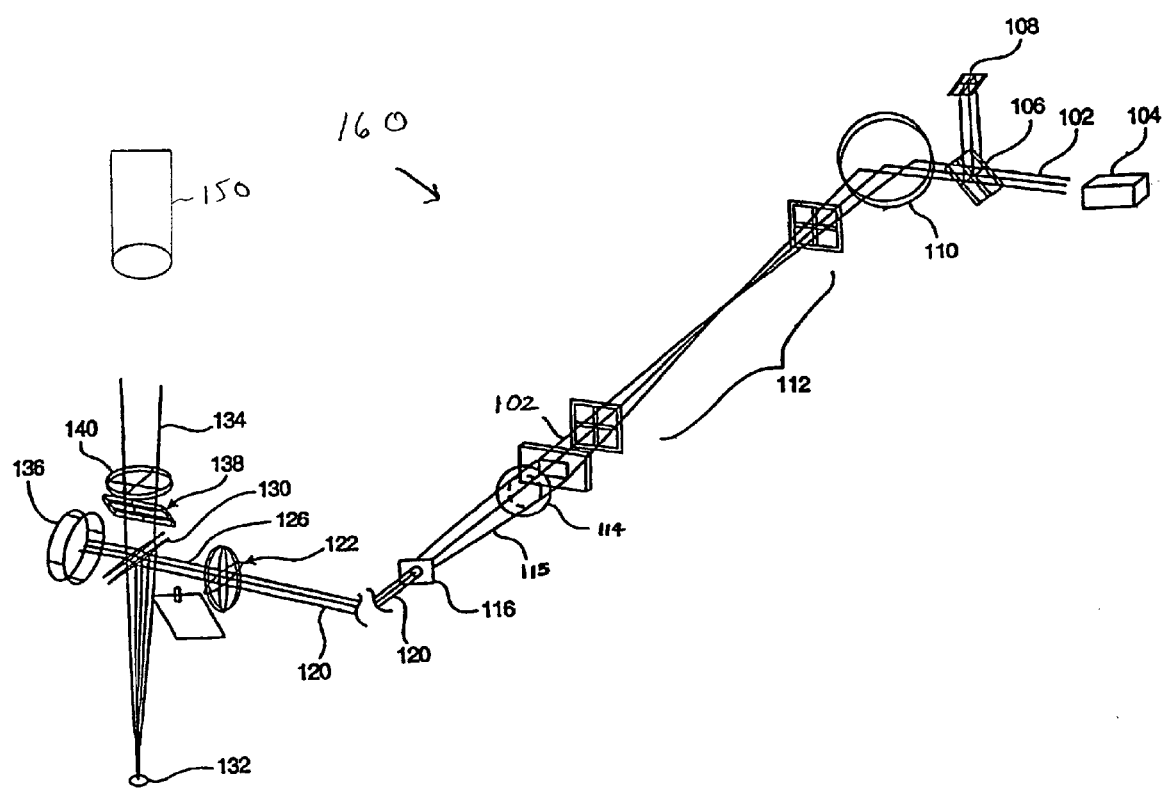

FIG. 1D schematically illustrates an embodiment of beam delivery system 160. A beam 102 is generated from a suitable beam source 104, such as an argon fluoride (ArF) excimer laser beam source for generating a laser beam in the far ultraviolet range with a wavelength of about 193 nm. Beam 102 is directed toward a beam splitter 106. A portion of beam 102 is reflected onto an energy detector 108, while the remaining portion is transmitted through beam splitter 106. Reflective beam splitter 106 may include a transmitting plate of partially absorbing material to attenuate the beam. Transmitted beam 102 is reflected by an adjustable mirror 110 that is used to align the path of the beam. In alternate embodiments, a direction of the beam path may be controlled with adjustable prisms. Beam 102 reflects from the mirror 110 onto a rotating temporal beam integrator 112 that rotates a path of the beam. Another type of temporal beam integrator may be used to rotate the beam.

Beam 115 travels to the spatial integration plane at which a variable diameter aperture 116 is disposed. In some embodiments, aperture 116 is a circular aperture. The spatial integration plane is disposed near the focal point of the positive lens 114. An apertured beam 120 emerges from the variable aperture 116. The variable aperture 116 may be a variable diameter iris, optionally combined with a variable width slit (not shown) used to tailor the shape and size profile of the beam 115 to a particular application, such as an opthalmological surgery procedure. The apertured beam 120 is directed onto an imaging lens 122, which may be a biconvex singlet lens with a focal length of about 125 mm. In some surgical embodiments, the beam 126 emerging from the imaging lens 122 is reflected by a mirror/beam splitter 130 onto the surgical plane 132, and the apex of the cornea of the patient is typically positioned at or near the surgical plane 132. Imaging lens 122 may be moved transverse to the beam to offset the imaged beam in order to scan the imaged beam about the surgical treatment plane 132. A treatment energy detector 136 senses the transmitted portion of the beam energy at the mirror/beam splitter 130. A beam splitter 138, a microscope objective lens 140, and the imaging device 150 form part of the observation optics. The beam splitter may be coupled to the imaging device 150 to assist in iris calibration as well as for viewing and recording of the surgical procedure. A heads-up display may also be inserted in the optical path 134 of the microscope objective lens 140 to provide an additional observational capability. Other ancillary components of beam delivery system 160 such as the movable mechanical components driven by an astigmatism motor and an astigmatism angle motor, are not shown to avoid prolixity.

Figure 1E:
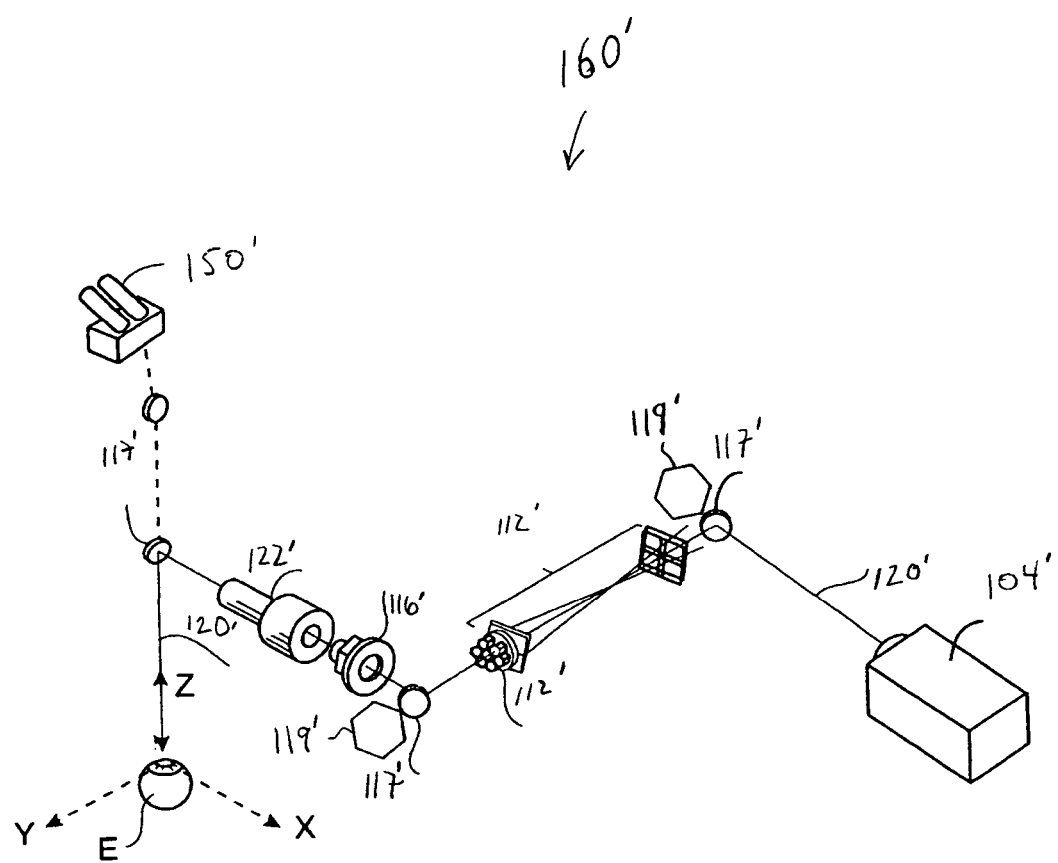

In another embodiment as schematically illustrated by FIG. 1E, beam delivery system 160' may include beam source 104', mirrors 117', spatial and temporal integrators 112', a variable aperture 116', and a scanning mechanism 122'. In some embodiments, scanning mechanism 122' can be configured to selectively deflect beam 120' laterally across the corneal surface of eye E in the X-Y plane. In some cases, scanning mechanism 122' may laterally deflect beam 120' in response to movement of eye E. Although certain aspects of FIGS. 1D and 1E are described in terms of a surgical application, it is appreciated that beam delivery systems 160 and 160' may represent a component of a non-surgical system as well. In some embodiments, electromechanical transducers such as galvanometers can be used to control movement of one or more components of beam delivery system 160 and 160'. For example, as depicted in FIG. 1E, a galvanometer 119' can be used to produce rotary movement in a deflection mirror 117' or other beam directing element. In some embodiments, galvanometers 119' can be used to adjust mirror 117' positioning so as to provide alignment of beam according to or relative to an intended pattern. Similarly, a computer controller may scan a beam by pivoting mirrors 117' using galvanometric motors 119', or any of a variety of other scanning mechanisms.

Figure 2A:
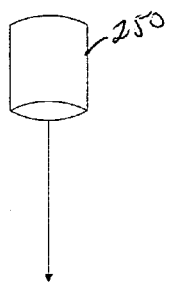
Figure 2A:

FIG. 2A illustrates an exemplary embodiment of an imaging device 250 and a calibration pattern 230. Calibration pattern 230 typically has known spatial dimensions and a known positional and angular orientation, where such orientation is often known relative to imaging device 250. For example, calibration pattern 230 may be disposed at a known image location, and may be imaged in any of a variety of positions and planes. In some cases, calibration pattern 230 may include a cross-hair or other feature to evaluate the perpendicularity of imaging device 250. Such features may be useful in calibrating the axis of imaging device 250 or otherwise evaluating rotational offsets. Any of a variety of trackers can also be used to evaluate XY or torsional movement or orientation. In the embodiment shown here, calibration pattern 230 includes a pattern of 9 (3×3) calibration spots. It may be desirable to set the illumination to a certain level prior to capturing any images with imaging device 250. Calibration pattern 230 may include a reticle or other optical element having lines, grids, spots, or other patterns. For example, calibration pattern 230 may include a pattern of 16 (4×4) spots, of 25 (5×5) spots, and the like. In some embodiments, calibration pattern 230 may include a series of marks 231 such as one or more circular chrome layers, each having a 10 mm or other known diameter, disposed on a surface 233 such as a glass or crystal plate. The captured image of the calibration pattern can represent, for example, the vertical and horizontal dimensions of each mark 231, and as described elsewhere herein, images of a test pattern may be rescaled according to the relative dimensions of the image of calibration pattern 230. Relatedly, the use of the image of calibration pattern 230 allows the various attributes of imaging device 250 to be quantified. Imaging device 250 attributes may include, for example, magnification, three dimensional position, angular orientation, and the like. In some embodiments, where calibration pattern 230 is disposed at an image location 235 or measurement plane, imaging device 250 can acquire an image of calibration pattern 230 so as to establish a link or association between imaging device pixels or sensors and the distance between imaging device 250 and image location 235. In some cases, calibration pattern 230 may be used to establish a calibration factor based on pixels per unit distance. Relatedly, imaging device 250 will often not have a fixed relationship between pixel counts or size and a size or scale of an object being imaged at the image location, so that, for example, a 0.1 mm$^2$ object in the center of the viewing field may correspond to and be imaged onto 9 (3×3) pixels in the center of an image sensor of imaging device 250, and may correspond to only 4 (2×2) pixels in one peripheral corner of the viewing field. Further, imaging device 250 may be responsible for some distortions of the calibration pattern image, which may also vary across the viewing field. Hence, the image of calibration pattern 230 may be fit to a modification algorithm to account for such imaging device distortion. In some embodiments, an operator may move calibration pattern 230 to a desired plane so that a sharp image may be obtained for calibration purposes.

Figure 2B:
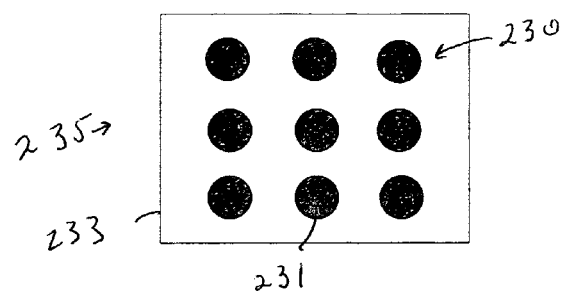
Figure 2B:
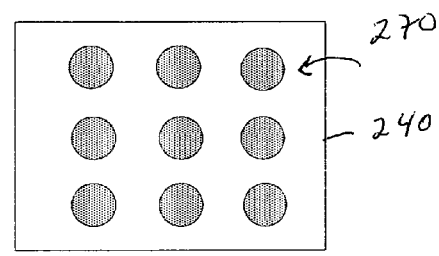
Figure 2C:
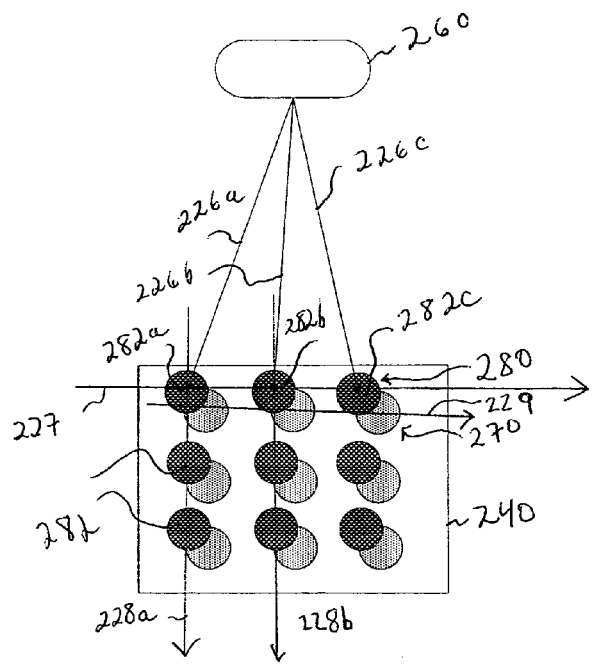

FIG. 2B illustrates an embodiment of an intended pattern 270 which beam delivery system 260 is configured to create on a test surface 240. It is appreciated that in many embodiments intended pattern 270 is not actually imageable or visible on test surface 240. In this sense, intended pattern 270 may represent a pattern which beam delivery system 260 is configured to create. In some embodiments, intended pattern 270 may correspond to a set of beam placement or positional parameters of beam delivery system 260, and may reflect intended dimensions or offsets. FIG. 2C illustrates an embodiment of an imageably altered test pattern 280 produced on test surface 240 according to intended pattern 270. In some embodiments, creation of test pattern 280 involves setting beam direction parameters of beam delivery system 260 according to intended pattern 270, directing a beam toward test surface 240 along beam path 226a to create an individual test spot 282a, adjusting beam direction parameters of beam delivery system 260 according to intended pattern 270, directing the beam toward test surface 240 along beam path 226b to create an individual test spot 282b, adjusting beam direction parameters of beam delivery system 260 according to intended pattern 270, directing a beam toward test surface 240 along beam path 226c to create an individual test spot 282c, and so on, so as to create test pattern 280. In some embodiments, procedures such as these may involve optics of beam delivery system 260 scanning the beam over tissue of an eye according to instructions from a computer, which may be encoded to correlate with intended pattern 270.

As beam moves from beam path 226a to beam path 226b, the beam can be described as being laterally redirected along an axis 227 from a first region to a second region, and as beam moves from beam path 226b to beam path 226c, the beam can be described as being laterally redirected along axis 227 from the second region to a third region. In some embodiments, axis 227 may correspond to a test pattern axis. In FIG. 2C, test pattern 280 is shown as deviating from intended pattern 270. Typically, this deviation is due to one or more beam system characteristics of beam delivery system 260, which may include alignment parameters or optical parameters, such as a lateral redirecting characteristic. In some embodiments, alignment parameters may include rotational offset, axial deflection offset, tilt, or other warping factors associated with beam delivery system 260. In related embodiments, optical parameters may include mirror thickness offset or pincushion effect. In some embodiments, such beam system characteristics can be referred to as beam positional or placement parameters.

Test surface 240 may be constructed on any of a variety of materials, including, for example, a silkscreen or luminescent material. Individual marks 282 or test spots may be characterized by a permanent change in color, a luminescent glow, a disrupted surface characteristic, and the like. For example, a luminescent material may include a piece of glass, crystal, or polymer that is optically activated, such as chromium doped, and has a relatively long luminescent lifetime. Images may be recorded after each beam pulse, wherein the luminescence of mark 282 may have decayed before the next beam pulse is directed onto the luminescent surface. Other types of test surface materials include photosensitive materials, photoreactive materials, photographic materials, Zapit paper, polymers that change color based on temperature, and polymethylmethacrylate materials. Individual marks 282 may include an ablation, a permanent change in color, a luminescent glow, and the like. In some embodiments, test surface 240 includes a photosensitive material, and marks 282 include a permanent change in color, such as a white spot on a black background or vice versa, or a luminescent glow. In some embodiments, test surface 240 includes a photoreactive material, a polymethylmethacrylate material, or other VISX calibration material, available from VISX, Incorporated of Santa Clara, Calif. For example, marks 282 may be ablated on a polymethylmethacrylate material with a laser beam.

Figure 2D:
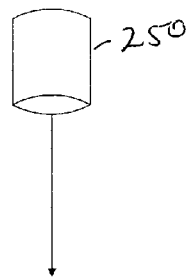
Figure 2D:
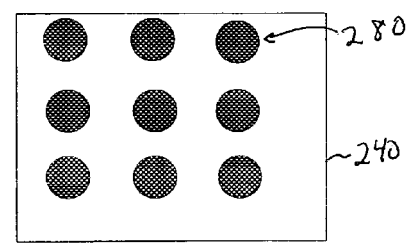

As seen in FIG. 2D, imaging device 250 can be used to image test pattern 280. Beam delivery system 260 can then be qualified or calibrated, in response to the test pattern image. In some embodiments, with reference to FIG. 2C, beam delivery system 260 may laterally redirect the beam along an axis 228 a plurality of times. Beam delivery system 260 can be calibrated by altering machine readable code of the beam system so that subsequent lateral deflections of the beam along axis 228a are determined using a plurality of different calibration factors associated with different beam locations along axis 228. In some embodiments, axis 228a may intersect axis 227. In related embodiments, beam delivery system 260 may laterally redirect the beam along axis 227 from a first region to a second region, and laterally redirect the beam along axis 228b from the second region to a third region. Beam delivery system 260 can be calibrated by altering machine readable code of the laser eye surgery system so that subsequent lateral deflection of the beam along axis 227 is determined using a first calibration factor, and so that subsequent lateral deflection of the beam along axis 228b is determined using a second calibration factor. The second calibration factor may be different than the first calibration factor. In another embodiment, beam delivery system 260 can laterally redirect the beam along a test pattern axis 227 of test pattern 280 from a first region to a second region, and the qualifying or calibrating of the beam can be based on an offset between test pattern axis 227 and an intended axis 229 of intended pattern 270. In some cases, the offset is an angular offset. In a further related embodiment, beam delivery system 260 laterally redirects the beam along a first test pattern vector between the regions of test pattern 280, and laterally redirects the beam along a second test pattern vector between the regions of test pattern 280. Qualification or calibration of beam delivery system 260 can be based on offsets between the vectors and intended vectors between regions of intended pattern 270. In still another related embodiment, a laser eye system can be calibrated by altering machine readable code of the laser eye surgery system in response to a first lateral beam deflecting characteristic of beam delivery system 260, and qualifying the laser eye surgery system by enabling use of the laser eye surgery system in response to a second lateral beam deflecting characteristic of beam delivery system 260 being within an acceptable threshold tolerance.

Figure 2E:
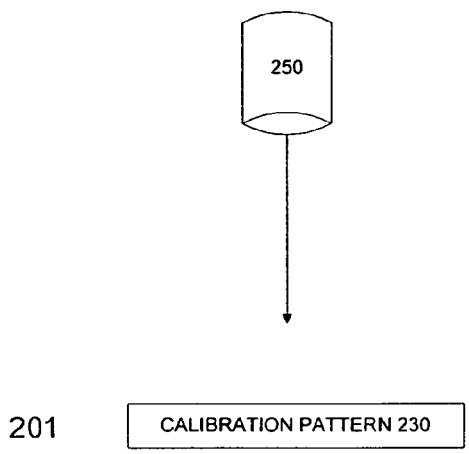
Figure 2F:
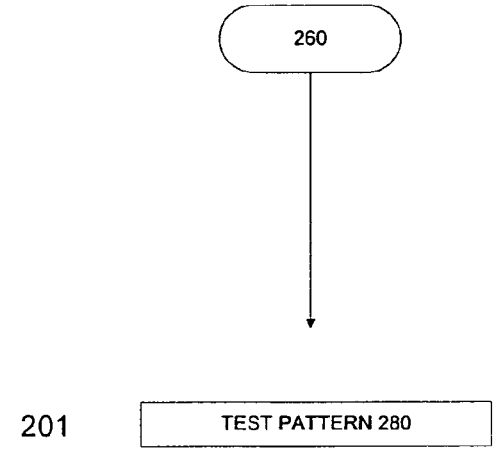
Figure 2F:
Figure 2F:
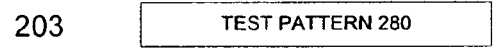
Figure 2G:
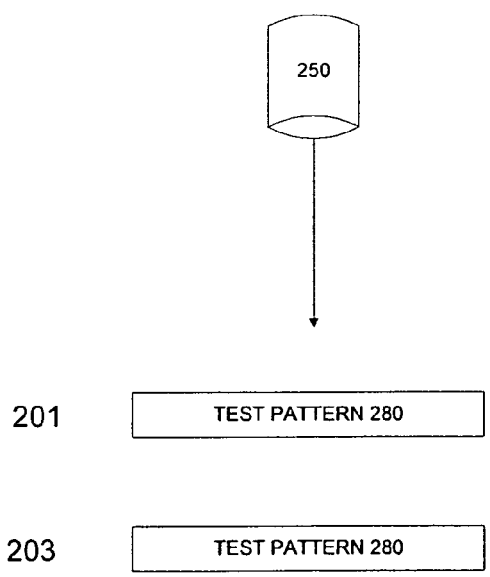

As seen in FIG. 2E, in some embodiments, calibration pattern 230 may be imaged at or near a beam focus plane 201 or at or near a treatment plane 203. Either of these planes, or any plane substantially near or between these planes, may be considered as a measurement plane. In some embodiments, the plane at which calibration pattern 230 is imaged, the plane at which test pattern 280 is created, and the plane at which test pattern 280 is imaged, may all be at the same plane. In some cases, treatment plane 203 may be a few millimeters or some other desired distance away from beam focus plane 201. As seen in FIG. 2F, in some embodiments, a beam can be oriented toward a beam focus plane 201 so as to produce test pattern 280 at beam focus plane 201. Optionally, test pattern 280 may be produced at treatment plane 203. As seen in FIG. 2G, test pattern 280 may be imaged by imaging device 250 at beam focus plane 201 or at treatment plane 203. In such cases, the captured image may be slightly out of focus if imaging device 250 is oriented toward treatment plane 203. In some cases, creation of test pattern 280, and imaging of calibration pattern 230 or test pattern 280 can be automatically implemented without operator intervention.

A fitting routine can accurately and precisely estimate the center position of beam. In some embodiments, calibration pattern 230 is imaged prior to directing the beam onto test surface 240, and test pattern 280 parameters may be calculated as the qualification and calibration procedure advances.

Image Processing

The location of an individual test spot image in a test pattern image can be described using centroid detection. In some embodiments, a center of mass for an image F(j,k) of size J×K can be represented with the following formula.

$$X \text{ Centroid} = C_x = \frac{\frac{1}{K}\sum_{j=1}^{J}\sum_{k=1}^{K}x_k F(j,k)}{\sum_{j=1}^{J}\sum_{k=1}^{K}F(j,k)},$$

$$Y \text{ Centroid} = C_y = \frac{\frac{1}{K}\sum_{j=1}^{J}\sum_{k=1}^{K}y_j F(j,k)}{\sum_{j=1}^{J}\sum_{k=1}^{K}F(j,k)}$$

A priori knowledge of the number and location of the individual spots of intended pattern 270 can be used to automate centroid detection of multiple test spot images within a single test pattern image. An individual test spot image centroid can be represented as $C_N=\{C_x, C_y\}$. In some embodiments, test spots 282 can be disposed toward the outer extremes of imaging device's field of view, thus enhancing the ability describe the performance of beam delivery system 260.

Scaling Calibration

As noted above, imaging device 250 can acquire an image of calibration pattern 230 so as to establish a link or association between imaging device pixels and the distance at an image location or measurement plane. Test pattern 280 can be created at the same plane, and Measurement Scale Factors $M_X$ and $M_Y$ can be computed by averaging the horizontal and vertical spot distances and then normalizing them by their intended displacements. These scale factors can be used to adjust Calibration Scale Factors $S_{CX}$ and $S_{CY}$ according to the following formula:

$$\begin{bmatrix} S_{ex}^i \\ S_{ey}^i \end{bmatrix} = \begin{bmatrix} M_x & 0 \\ 0 & M_y \end{bmatrix} \begin{bmatrix} S_{ex}^0 \\ S_{ey}^0 \end{bmatrix}$$

where $S_{ex}^o$ and $S_{cy}^o$ represent an intended design specification, and $S_{ex}^i$ and $S_{cy}^i$ represent an updated calibrated scale. In some embodiments, this formula can relate beam deflection in units of distance to that of motor counts for controlling various components, such as galvanometers, of beam delivery system 260.

Rotational Offsets

One approach to establish rotational orientation involves calibrating imaging device 250 in angular space using a reference marking from a calibration pattern 230 such as a precision reticle or target. The rotational offset measured in test pattern 280 can then be compared to the known rotational offset of imaging device 250. If desired, rotational transformations can be performed. In some embodiments, a limit can be specified for the magnitude of difference between rotational offsets to disqualify a defective scanning system.

Axial Deflection Offset Error

If beam delivery system 260 uses reflecting surfaces to steer the beam, then offsets in deflection from the true axis of rotation may introduce nonlinearities or other complex direction effects. In some embodiments, such an error may be a function of the distance between the true axis and the reflecting surface (T) and the alignment of the entry beam with respect to the axis of rotation (K). The error may be represented by the following formula.

$$E = \frac{T - K\sin\alpha}{\cos\alpha}$$

Similar approaches are discussed by Gerald F. Marshall in *Optical Scanning*, page 561 (1991). If beam delivery system 260 operates within a narrow angular range, then the errors introduced due to surface offset may be extremely linear and may be accounted for by this calibration method directly, obtaining as much accuracy as imaging device 250 resolution provides. Optionally, the above relationship can be used to determine if the alignment of the beam onto the turning mirrors is outside a specified amount An exemplary embodiment of a axial deflection offset error is depicted in FIG. 2H, which shows a test pattern 280h axially offset from an intended pattern 270h on a test surface 240h.

FIGS. 2I and 2J depict a comparison between a linear offset and a nonlinear offset. An intended pattern 270i and a corresponding test pattern 280i are shown on a test surface 240i in FIG. 2I. The relationship between intended pattern 270i and test pattern 280i can be illustrated graphically by FIG. 2J. The horizontal axis $(X_i)$ represents lateral displacement in the intended pattern along the x direction, when viewing test surface 240i. The vertical axis $(X_t)$ represents lateral displacement in the test pattern along the x direction, when viewing test surface 240i. The solid curved line NL represents the nonlinear relationship of intended pattern 270i and test pattern 280i as shown in FIG. 2I. The dashed straight line L represents a hypothetical linear relationship between an intended pattern and a test pattern.

Pincushion Error

Figure 2K:
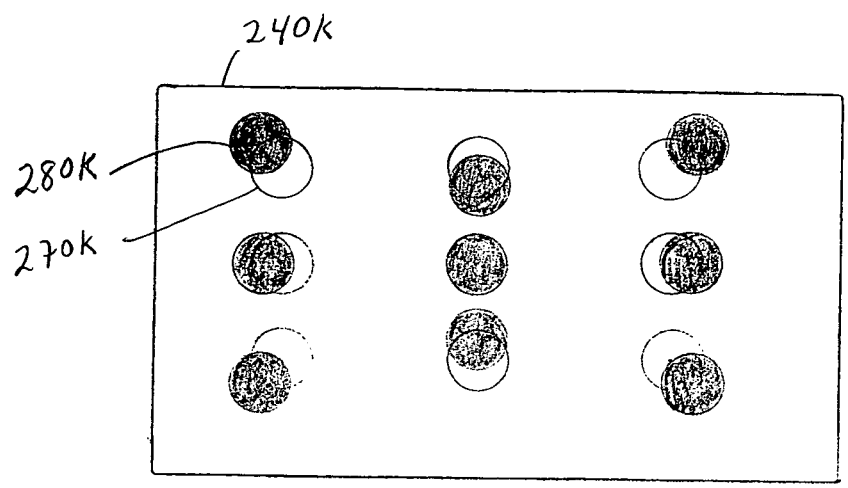
Figure 2L:
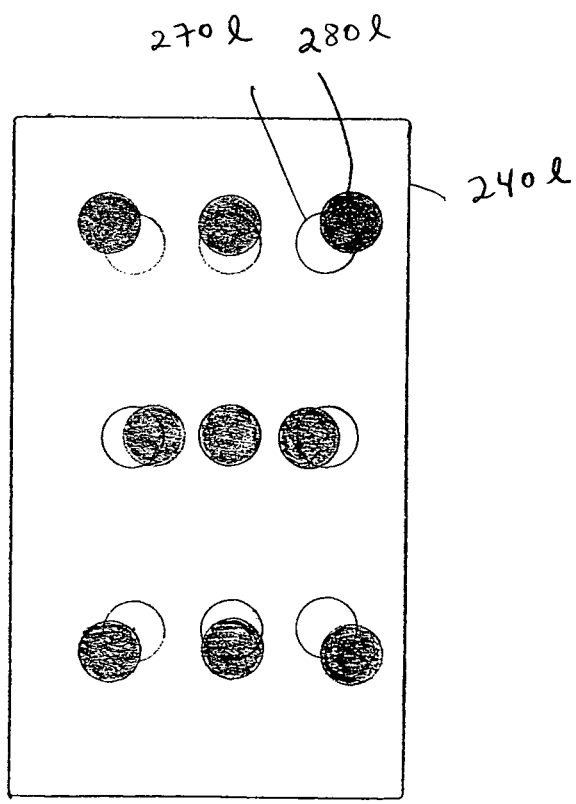

When the scanning operation is separated by axis, deflections propagated from the first mirror to the second can introduce a one dimensional distortion in the scanning direction corresponding to the first axis onto the imaging plane. The change of a large-offset intended position from the first mirror $(Y_t)$ as the second mirror angle changes $(\theta_x)$ can be represented relatively by the following formula $$\varepsilon = \frac{Y_{i\theta x} - Y_{i0}}{2Y_{i0}} = \frac{1 - \cos\theta_x}{2(1 + e/d)\cos\theta_x}$$

where e represents the spacing between the mirrors and d represents the distance from the last mirror surface to the image plane. Similar approaches are discussed by Gerald F. Marshall in *Optical Scanning*, page 568 (1991). In some embodiments, mirror angle changes may be sufficiently small such that pincushion effects may be ignored. Correcting for this pincushion error may in some cases be limited by the resolution of the imaging device or measurement camera. FIGS. 2K and 2L illustrate embodiments pincushion offsets, showing intended patterns 270k and 270l, and test patterns 280k and 280l, on test surfaces 240k and 240l, respectively.

Checking for Alignment Errors

As described above, rotational alignment errors can be checked against a fixed target imaged by the imaging device or camera. For tilt errors to be detected, it is helpful to know that the plane of investigation for imaging the test spots (e.g. the surface of the material ablated) is in the correct position. Linear trends in the measured distances of the spots from left-to-right or top-to-bottom during the Scaling Calibration can be used to detect whether the scanner system is tilted. Other errors in the alignment of the optics may be detectable by the amount of error not accounted for in the linear scaling transformation. In addition to tilt, other warping factors may be measurable that may indicate artifacts such as spherical aberration.

TABLE 1 illustrates an exemplary qualification and calibration matrix. A beam delivery system may be qualified or calibrated based on certain observed or calculated beam delivery system characteristics, such as a lateral redirecting characteristic.

TABLE 1

|  | Scaling | Rotation | Axial Deflection | Pincushion |
| --- | --- | --- | --- | --- |
| Qualification | disqualify system if scale exceeds certain limits | disqualify system if rotation exceeds certain limits | disqualify system if deflection exceeds certain limits | disqualify system if pincushion effect exceeds certain limits |
| Calibration | calibrate system if scale is within specified limits | calibrate system if rotation is within specified limits | calibrate system if deflection is within specified limits | calibrate system if pincushion effect is within specified limits |

It is appreciated that some embodiments may avoid disqualification by coupling certain calibration axes (e.g. x axis and y axis), so that angular errors or offsets result in adjustments to both axes.

Figure 3A:
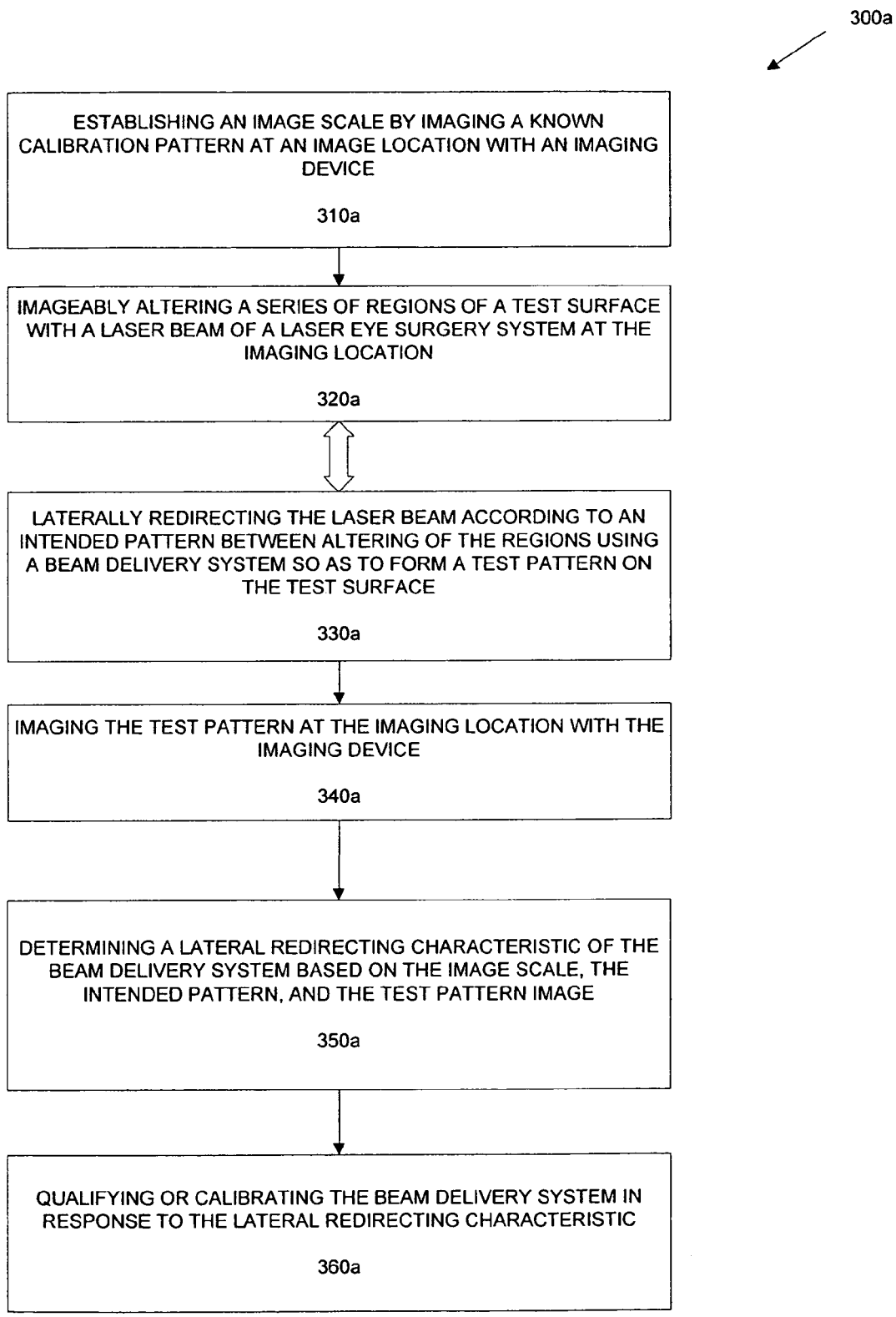

FIG. 3A illustrates an exemplary method for testing a laser eye surgery system. The method can include imaging a known calibration pattern at an image location with an imaging device, and establishing an image scale based on the calibration pattern and the calibration pattern image as depicted in step 310a. The method also typically includes imageably altering a series of regions of a test surface with a laser beam of the laser eye surgery system at the imaging location, as depicted in step 320a, and laterally redirecting the laser beam according to an intended pattern between altering of the regions using a beam delivery system so as to form a test pattern on the test surface, as depicted in step 330a. In step 340a, the test pattern is imaged at the imaging location with the imaging device. In step 350a, a lateral redirecting characteristic of the beam delivery system is determined based on the image scale, the intended pattern, and the test pattern image. The beam delivery system can be qualified or calibrated in response to the lateral redirecting characteristic, as shown in step 360a.

FIG. 3B illustrates an exemplary method 300b for qualifying and calibrating a beam system. A beam system typically includes components such as a beam source, a beam delivery system, or both. The method can include establishing an image scale by imaging a calibration pattern at an image location, as depicted by step 310b. Step 320b involves imageably altering a test surface with a beam system according to an intended pattern to produce a test pattern on the test surface. In step 330b, the test pattern is imaged with an imaging device. Step 340b includes determining a beam system characteristic based on the image scale, the intended pattern, and the test pattern image. Step 350b is characterized by the decision of determining if the beam system characteristic is within specified qualification limits. If the beam system characteristic is not within specified qualification limits, the beam system may be disqualified based on the beam system characteristic, as shown in step 360b. For example, a rotation effect of the beam delivery system may be too excessive. If the beam system characteristic is within specified qualification limits, the beam system may be qualified based on the beam system characteristic, as shown in step 370b. After the beam system is qualified, a decision is by determining if the beam system characteristic is within specified calibration limits, as shown in step 380b. Step 390b illustrates the outcome when the beam system characteristic is within specified calibration limits, and typically involves proceeding with operation of the beam system. In some embodiments, this can involve treating a patient with the beam system. For example, upon qualification or calibration, a patient's cornea may be ablated to correct a variety of vision defects, including myopia, hyperopia, astigmatism, and other corneal surface profile defects.

Step 395b illustrates the outcome when the beam system characteristic is not within specified calibration limits, and typically involves adjusting certain components of the beam system. Such adjustments can be system-specific. Relatedly, such adjustments can be made so as to individually and independently alter the position of each of the test spots of a subsequent test pattern created by the beam delivery system. After the beam system has been calibrated, it can be tested again, beginning with step 320b. In some cases, it may be possible to calibrate and then use the system, without retesting.

It is appreciated that some embodiments may include both the qualification and calibration steps, some embodiments may include only the qualification steps, and some embodiments may include only the calibration steps. Calibration or adjustment may involve changing a drive signal for an actuator, for example a galvanometer which controls placement of a beam delivery system mirror. Such drive calibrations may also be variable drive calibrations. In some aspects, a calibration may not involve a change in beam delivery system hardware, but may involve an adjustment in a signal correlation.

Analysis of the test pattern may be automated using the systems described herein. In some laser ablation embodiments, the computer may indicate whether the beam delivery system is sufficiently accurately calibrated to perform any ablation, or to perform a particular photorefractive resculpting. The computer system may optionally adjust the ablation algorithm based on the actual position of the test pattern, either automatically or with manual input, to avoid or attenuate an unwanted beam delivery system characteristic, for example. Hence, the system can provide a feedback mechanism to enhance the accuracy of the change in corneal shape effected by a laser.

In some cases, a given beam system characteristic may vary in direct proportion to adjustment of a beam delivery system component. For example, adjustment of the position or rotation of a mirror of the beam delivery system may result in a corresponding change in the positioned beam trajectory. In other aspects, a given beam system characteristic may vary in a non-linear fashion in response to adjustment of a beam delivery system component. Beam delivery system performance data can be collected so as to produce interpolation curves, fitting curves, charts, look-up tables, and other similar means for determining or representing a relationship between a beam system characteristic or positional parameter and a beam delivery system configuration. For example, a look-up table may be created based on an intended pattern and a test pattern, and standard interpolation routines may be used between discrete table entries. Such curves or charts may be useful in the qualification and calibration techniques described herein.

A drift of the beam delivery system may be determined by monitoring a variance in a test pattern. It will be appreciated that drifts may be dependent upon several factors, such as the manner in which the system is used between measurements, the particular set of system parameters, changes in environmental conditions such as temperature, and the like. Embodiments of the present invention can also be applied to judge the stability of the beam delivery system. For example, the test surface may include a luminescent plate. After each beam pulse, an image is captured while the plate is still emitting light. Images are then analyzed. Positions of test spots can be calculated and plotted on x and y axes so that the plot provides a map of where the beam pulses landed. This plot can then be used to determine any systematic movement of the laser beam with time. Alternatively, the data can be used to determine parameters such as the statistical variations in x and y positions. In some embodiments, a beam delivery system may be qualified or calibrated on the basis of drift.

Referring back to FIG. 1D, a number of the optical elements in beam delivery system 60 may be rotated along the beam delivery path, as described in detail in U.S. Pat. No. 6,816,316, the disclosure of which is hereby incorporated by reference, to distribute any distortion caused by imperfections of the optical elements. In one embodiment, the lens 114 is rotated around its axis. In other embodiments, the beam splitter 106 may be moved along its plane; the mirror 110 may be moved along its plane; the diffractive optic 113 may be moved in its plane, and the mirror/beam splitter 130 may be moved along its plane. Although the path of the beam is stable with respect to movement of an optical element, minor deviations in the position of the optical center about the axis of rotation may occur, and such deviations may induce a slight wobble in the path of the laser beam as the optical element rotates. Advantageously, the techniques described herein may also be utilized to identify a rotation-induced laser induced wobble from a plurality of marks. Analysis of images of the marks may help account for these small deviations due to rotation of the optical element.

FIG. 4 illustrates an exemplary method 400 for determining a beam delivery system characteristic 490 by inputting a variety of variables or measurements. For example, the beam delivery system characteristic can be based on one or more of a calibration pattern parameter 410, a calibration pattern image 420, an intended pattern parameter 430, a test pattern image 440, a position of an imaging device 450, a position of a calibration pattern 46, a position of a test pattern 40, and a position of a beam delivery system 480. It is understood that the position of each of these components can be considered in terms of a location, an angular disposition, or any other orientation in three dimensional space.

It will be appreciated that the presently disclosed qualification and calibration systems and methods will find use in a variety of different laser systems, including scanning lasers and large area laser ablation systems. Examples include the VISX STAR™, STAR S2™, STAR S3™, STAR S4™ Excimer Laser Systems™, and laser systems employing wavefront technologies, all of which are commercially available from VISX, Incorporated of Santa Clara, Calif. Other laser systems include those available from Alcon Summit, Autonomous Technologies Corp., Bausch & Lomb, Chiron Vision, LaserSight, Nidek Co., Ltd., Zeiss Meditec, Schwind, Wavelight Technologies, and a variety of other companies.

The techniques described herein may be used to analyze a variety of radiation beams such as ultraviolet, gamma, and x-ray beams, may be used with a wide variety of ablation planning protocols or algorithms, and may provide input to such algorithms which can enhance their accuracy. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Treatments that may benefit from the invention include intraocular lenses, contact lenses, spectacles and other surgical methods in addition to refractive laser corneal surgery. Therefore, although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A method of testing a laser eye surgery system, comprising:

imaging a known calibration pattern at an image location with an imaging device;

establishing an image scale based on the calibration pattern and the calibration pattern image;

imageably altering a series of regions of a test surface with an ablation laser beam of the laser eye surgery system at the imaging location;

laterally redirecting the laser beam according to an intended pattern between altering of the regions using a beam delivery system so as to form a test pattern on the test surface;

imaging the test pattern at the imaging location with the imaging device;

determining a lateral redirecting characteristic of the beam delivery system based on the image scale, the intended pattern, and the test pattern image; and qualifying or calibrating the beam delivery system in response to the lateral redirecting characteristic, wherein the beam delivery system laterally redirects the beam along a first axis from a first region to a second region, and laterally redirects the beam along a second axis from the second region to a third region, and wherein the beam delivery system is calibrated by altering machine readable code of the laser eye surgery system so that a subsequent lateral deflection of the beam along the first axis is determined using a first calibration factor, and so that a subsequent lateral deflection of the beam along the second axis is determined using a second calibration factor, the second calibration factor being different than the first calibration factor.

2. The method of claim 1, wherein the beam delivery system laterally redirects the beam along a second axis a plurality of times, and wherein the beam delivery system is calibrated by altering the machine readable code of the laser eye surgery system so that subsequent lateral deflections of the beam along the second axis is determined using a plurality of different calibration factors associated with different beam locations along the second axis, the second axis intersecting the first axis.

3. The method of claim 1, wherein the beam delivery system laterally redirects the beam along a first test pattern axis of the test pattern from a first region to a second region, and wherein the qualifying or calibrating of the beam comprises identifying an offset between the test pattern axis and an intended axis of the intended pattern.

4. The method of claim 3, wherein calibrating the beam comprises altering machine readable code of the laser eye surgery system so that a subsequent lateral deflection of the beam along the first test pattern axis is determined based on the offset.

5. The method of claim 3, wherein qualifying the beam comprises enabling use of the laser eye surgery system in response to the offset being below an acceptable tolerance.

6. The method of claim 3, wherein the offset comprises an angular offset.

7. The method of claim 1, wherein the beam delivery system laterally redirects the beam along a first test pattern vector between the regions of the test pattern, and laterally redirects the beam along a second test pattern vector between the regions of the test pattern, and wherein qualification or calibration of the beam delivery system comprises determining offsets between the vectors and intended vectors between regions of the intended pattern.

8. The method of claim 1, further comprising calibrating the laser eye system by altering machine readable code of the laser eye surgery system in response to a first lateral beam deflecting characteristic of the beam delivery system, and qualifying the laser eye surgery system by enabling use of the laser eye surgery system in response to a second lateral beam deflecting characteristic of the beam delivery system being within an acceptable threshold tolerance.

* * * * *